(12) United States Patent
Milioto

(10) Patent No.: US 6,829,377 B2
(45) Date of Patent: Dec. 7, 2004

(54) LIMB EXTREMITY POSITIONING DEVICE AND MEASUREMENT METHOD

(75) Inventor: Giuceppe Milioto, 110. Longmore Drive, Pointe-Claire, Quebec (CA), H9S 5A3

(73) Assignee: Giuceppe Milioto, Pointe-Claire (CA)

(*) Notice: Subject to any disclaimer, the term of this patent is extended or adjusted under 35 U.S.C. 154(b) by 512 days.

(21) Appl. No.: 09/832,811

(22) Filed: Apr. 12, 2001

(65) Prior Publication Data

US 2001/0030297 A1 Oct. 18, 2001

(51) Int. Cl.[7] .................................................. G06K 9/00
(52) U.S. Cl. ....................... 382/128; 382/309; 382/291; 382/154; 33/3 R; 623/27
(58) Field of Search ........................... 33/3 R, 511, 512, 33/6, 3 A, 3 B, 3 C, 227, 228, 286, 515, 613, 645; 382/128, 308, 291, 285, 154; 128/922; 250/458.1; 356/39; 377/10; 623/27, 28, 29; 36/140

(56) References Cited

U.S. PATENT DOCUMENTS

| | | | |
|---|---|---|---|
| 4,662,079 A | 5/1987 | Graf et al. ..................... 33/512 |
| 4,735,754 A | 4/1988 | Buckner ..................... 264/40.1 |
| 4,819,660 A | 4/1989 | Smith .......................... 128/774 |
| 4,941,463 A | * 7/1990 | Hergenroeder ............... 602/39 |
| 5,128,880 A | 7/1992 | White ........................ 382/165 |
| 5,164,793 A | 11/1992 | Wolfersberger et al. .... 356/376 |
| 5,457,325 A | 10/1995 | Huberty ................. 250/559.29 |
| 5,671,055 A | 9/1997 | Whittlesey et al. ......... 356/376 |
| 5,689,446 A | 11/1997 | Sundman et al. ........... 364/560 |
| 5,695,453 A | 12/1997 | Neal .............................. 602/6 |
| 5,715,834 A | 2/1998 | Bergamasco et al. ....... 600/595 |
| 5,790,256 A | 8/1998 | Brown et al. ................ 356/376 |
| 5,804,830 A | 9/1998 | Shafir ..................... 250/559.22 |
| 5,911,126 A | 6/1999 | Massen ...................... 702/153 |
| 6,155,120 A | 12/2000 | Taylor ................... 73/862.046 |
| 6,177,171 B1 | 1/2001 | Constantinides ............ 428/101 |
| 6,282,258 B1 | 8/2001 | Stein et al. .................... 378/54 |
| 6,425,852 B1 | 7/2002 | Epstein et al. ................ 600/13 |
| 6,463,351 B1 | 10/2002 | Clynch ........................ 700/163 |
| 2002/0183615 A1 | 12/2002 | Bucholz ...................... 600/427 |

* cited by examiner

Primary Examiner—Bhavesh M. Mehta
Assistant Examiner—Barry Choobin
(74) Attorney, Agent, or Firm—Brouillette Kosie Prince

(57) ABSTRACT

A device is provided to support and position a limb extremity in a desired steady position to enable acquisition of morphological data from the underside and the upper portion of the limb extremity in a substantially non-weight-bearing attitude. The device comprises a stretchable envelope, made of a thin elastomeric membrane, and a support provided with adjustable positioning members such as hooks, pegs or clips comprising a proximal end and a distal end. The envelope is provided with laterally extending positioning member engaging portions disposed on opposite sides along the longitudinal axis of said envelope. Said positioning member engaging portions receive the distal end of said adjustable positioning members and thereby enable adjustable support and positioning of the envelope and, in turn, of the limb extremity inserted therein. There is further disclosed a measurement method comprising the steps of inserting a limb extremity into a closely fitted thin stretchable envelope provided with positioning member engaging portions, attaching adjustable positioning members to said portions, adjusting the position of said adjustable positioning members and performing optical acquisition of morphological data of the limb extremity.

13 Claims, 3 Drawing Sheets

LIMB EXTREMITY POSITIONING DEVICE AND MEASUREMENT METHOD

BACKGROUND OF THE INVENTION

1. Field of the Invention

The present invention relates to a positioning device for a limb extremity more particularly useful in supporting and positioning a foot. The device is particularly intended to set and maintain a foot in an appropriate position to carry-out a radiographic or external measurement procedure, or to take an imprint of the foot or amputation stump. The positioning device is principally characterised in that it allows simultaneous measurement of the top and underside portions of the foot in a "no-load" position, i.e. when the foot is not bearing on a supporting surface.

2. Brief Description of the Prior Art

Several systems have been developed for many years to measure the shape of a foot in order to fabricate a customised footwear article or an orthotic insole to be placed in a shoe or boot for comfort optimisation or therapeutic purpose. The best systems rely on contact-free techniques based on digital cameras, laser or LED scanners and computerised analysis systems to obtain an accurate three-dimensional mapping of the external envelope of the foot. These data are thereafter used to identify or manufacture footwear or orthotic or prosthetic that is best fitted to the foot or stump size and shape. To achieve optimal results or therapeutic objectives, an accurate 3D mapping of the underside of the foot is required in addition to the dimensional information on the upper portion of the foot. Only a few systems of the prior art provide such complete information, still with limited accuracy.

For example, U.S. Pat. No. 4,819,660 (Smith—1989) discloses an apparatus comprising a camera head rotated around an amputation stump in a circular path to provide multiple 2D images. The extremity of the stump is supported on a stool. U.S. Pat. No. 5,689,446 (Sundmann et al.—1997) an array of gauge pins is used to take the impression of the underside of the foot, while a 3D camera system first acquires the dimensional information of the top of the foot and secondly acquires the image of the conforming gauge pin array once the foot is removed. U.S. Pat. No. 5,457,325 (Huberty—1995) refers to a similar approach to reconstitute the complete outer shape of the foot. In U.S. Pat. No. 5,790,256 (Brown et al.—1998), LED arrays scan the sides of the feet while pressure sensitive arrays acquires data on the underside morphology of the feet. U.S. Pat. No. 5,128,880 (White—1992) teaches a method for measuring the underside of a foot comprising the steps of placing the foot against a reference surface within the scanning field of a scanner, scanning the foot bottom facing surface and displaying the scanned foot image articulating distances of portions of the foot bottom facing surface from the reference surface. However no measurement of the upper portion of the foot is performed in this method. In U.S. Pat. No. 5,164,793 (Wolfersberger et al.—1992) a foot is deposed on an inclined plate-glass and 3D information about the top portion is recorded from a laser and camera system, while a camera is taking a 2D image of the underside of the foot to calculate the key length and girth data to fit a shoe. In U.S. Pat. No. 5,671,055 (Whittlesey et al.—1997), a three-dimensional profile of the foot of a person standing on a surface is obtained by scanning one side after the other with a laser camera mounted on a turntable. Such a method obviously provides no information about the foot underside but its perimeter. In U.S. Pat. No. 5,804.830 (Shafir—1998), radiant-energy emitters and sensors are disposed about a circular ring moving along a foot positioned about the center of said ring. Three-dimensional mapping of the outer contour is obtained but with very low definition of the foot underside since the foot is deposed on supporting plate.

Although the above examples show that adequate contact-free measurement techniques exist to acquire complete dimensional data, no existing system is designed to provide direct contact-free three-dimensional measurement of the upper portion and underside of a foot, with the possibility of performing such measurements simultaneously to avoid distortions due to possible movement of the foot. An integral 3D system could be set-up by combination of certain of the existing techniques with still important limitations, mainly imputable to the foot supporting and positioning device, which introduces interference such as hidden foot areas and modification of the natural foot envelope. Indeed, these systems perform the measurement procedure while the person is standing on a usually transparent surface (fully loaded condition) or with the foot being deposed on an inclined surface in a semi-loaded condition. Hence, the so obtained measurements generally lack information about the underside of the foot and do not take into consideration the best foot behaviour for maximum comfort or therapeutic ends as a function of its global morphology and biomechanics i.e. bone structure, alignment, over or under-pronation, fatty padding etc.

It is a best approach in designing customised footwear and especially orthotics for the treatment of foot or postural deficiencies to base the conception on complete dimensional information acquired in the so-called "neutral unloaded position" of the leg and foot so to implement the appropriate correcting means. U.S. Pat. No. 4,662,079 delivered to Graf et al in 1987 provides a process and apparatus to align a leg and foot in the neutral position to take a physical imprint using plaster or a similar medium. The neutral position can be defined as the most efficient position to accommodate the full range of foot rotation during locomotion. Design of customised footwear and orthotic shall take that information into consideration and not only the dimensioning of the foot in stressed weight-bearing conditions, to allow the foot and body structure to behave with minimal stress and maximal comfort.

Today's techniques provide faster and more accurate means for gathering foot dimensioning data as aforementioned. It is nevertheless of prime importance, especially in designing athletic or therapeutic footwear, to be able to support the foot in a non-loaded condition and align and maintain it in a natural or neutral position while carrying-out the contact-free measurement. The supporting and positioning device shall therefore be of a type that will not interfere with the dimensional data acquisition process and permit three-dimensional contour mapping of underside and top portions of the foot in a non-loaded condition, with the possibility of scanning both foot portions simultaneously.

There is thus a need for a novel foot supporting and positioning device capable of maintaining the foot in a desired position in non-loaded conditions while causing negligible interference with contact-free optical measurement apparatus, even when the upper and underside portions of the foot are measured simultaneously, according to a preferred measurement method.

OBJECTS OF THE INVENTION

The present invention provides a foot supporting and positioning device and a measurement method advantageously used in co-operation with a contact-free optical three-dimensional measurement system which overcomes the limitations and drawbacks of the above mentioned solutions of the prior art, and more specifically:

- a first object of the instant invention is to provide a foot supporting and positioning device which totally or substantially relieves the underside of the foot from the pressure exerted by the weight of the person;
- a second object of the present invention is to provide a foot supporting and positioning device which leaves the top and underside portions of the foot free of obstruction for manual or optical acquisition of the three-dimensional measurement information;
- a third object of the present invention is to provide a foot supporting and positioning device comprising adjustable means to allow a specialist to position and maintain the foot in a natural or neutral or in any desired position while a measurement process is being carried-out, and without interfering with the process;
- a fourth object of the present invention is to provide a foot supporting and positioning device which closely adheres to the foot surface to provide a smooth surface, thus eliminating skin texture and small defects that would have to be corrected on a scanned outer contour image to avoid reproduction of such texture and defects in the insole or last to be fabricated from the acquired dimensional data;
- a fifth object of the present invention is to provide a foot supporting and positioning device where the membrane in contact with the foot surface is an inexpensive single-use throw-away stretchable thin membrane;
- a sixth object of the present invention is to provide a foot supporting and positioning device providing a separating surface between the upper and underside portions of the foot, thus preventing interference between a upper and a lower measurement apparatus;
- a further object of the present invention is to provide a foot measurement method using the foot supporting and positioning device of the present invention and allowing simultaneous optical measurement of the top and underside portions of a foot in a non-loaded condition;

SUMMARY OF THE INVENTION

More specifically, in accordance with the invention as broadly claimed, there is provided a foot supporting and positioning device comprising a stretchable envelope made of a thin elastomeric membrane and a support provided with adjustable support members such as hooks, pegs or clips comprising a proximal end and a distal end. The envelope is provided with two lateral wings disposed on opposite sides along the longitudinal axis of said envelope. Said lateral bands are flexible and substantially resistant to axial and lateral elongation and are provided with support member receiving portions such as perforations to receive the distal end of said adjustable members and thereby adjustably supporting and positioning the envelope and the foot inserted therein.

There is also disclosed a measurement method comprising the steps of inserting a foot in a closely fitted thin stretchable envelope provided with support member receiving portions, adjusting the position of said adjustable support members, connecting the sides of the envelope to said members and performing simultaneous or sequential optical measurement of the foot top and underside portions through the stretchable envelope.

BRIEF DESCRIPTION OF THE DRAWINGS

Similar reference numerals refer to similar parts throughout the various Figures.

DETAILED DESCRIPTION OF THE DRAWINGS

A preferred embodiment of the extremity supporting and positioning device according to the present invention will now be described in detail referring to the appended drawings.

Figure 1:
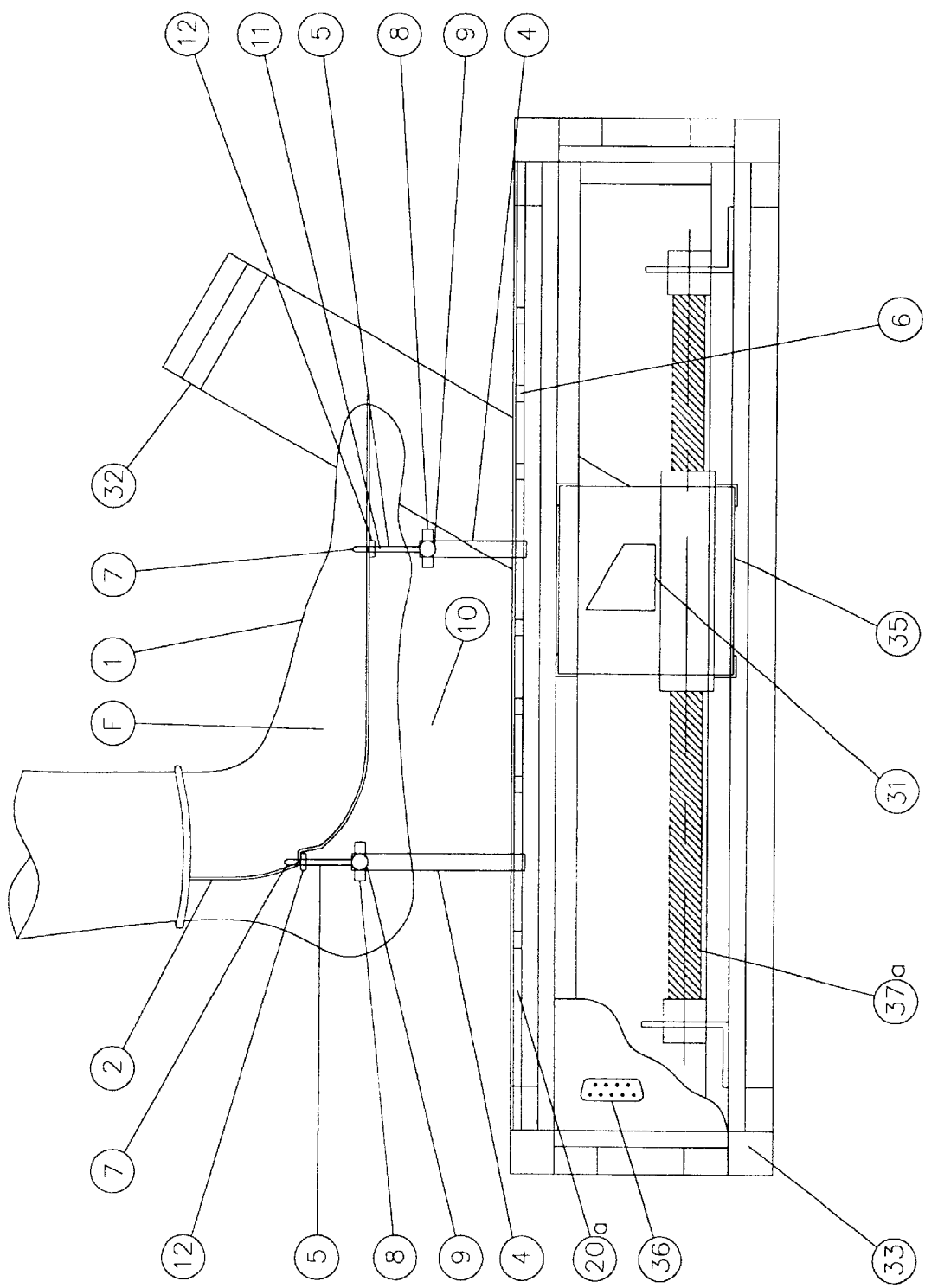
FIG. 1 is a side elevation view of a foot supported and positioned by the device of the present invention, showing the upper and lower heads of a measurement system.

Referring to FIG. 1, there is illustrated a patient's foot F supported and positioned using the device of the present invention. Although this illustration suggests that the patient's leg is supported horizontally with the foot in a non-weight-bearing position, a similar set-up would provide a semi-weight-bearing position of the foot in the case of a patient sitting on a chair with his/her legs suspended downwardly. In order to provide support without causing undesirable obstructions on the top and bottom portions of the foot to optical or ultrasonic scanning, a special envelope is installed on the foot F as a sock. The envelope 10 comprises a thin elastomeric membrane 1, preferably made of latex (dipped to an original thickness of about one sixteenth of an inch) to stretch and adapt perfectly to the surface of the foot. However, the membrane will prevent a scanning system from recording small defects and the details of the skin texture, thus avoiding some editing of the data as would be necessary to prevent reproduction of such defects in a last or insole made from said data. The envelope 10 further comprises semi-rigid lateral wings 2 incorporating an internal web preferably made of a plastic mesh 3, such as a Nylon mesh with an approximately 0.1 to 0.25 inch grid size. The mesh resists the stretching providing some stiffness to the wings and acting as supporting straps. Therefore, the mesh is preferably implemented as independent adjacent strips to allow for some extension of the envelope in order to adapt to the foot contour. The wings 2 are extending about one to two inches from the sides of the envelope 10 and are coated with the same elastomeric material as the membrane, according to the one step dip process.

Figure 2:
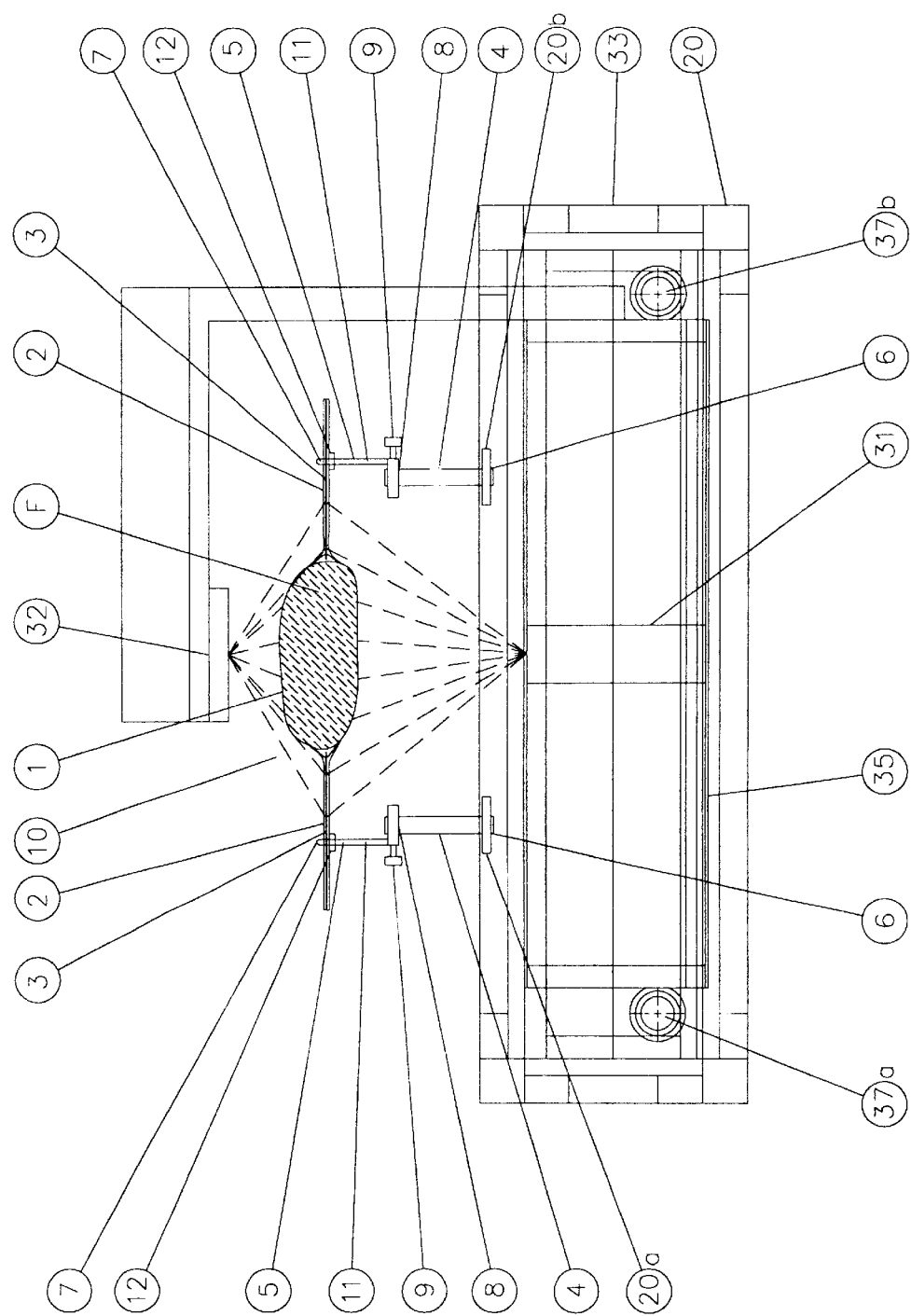
FIG. 2 is a cross sectional view of a foot supported and positioned by the device of the present invention.
Figure 3:
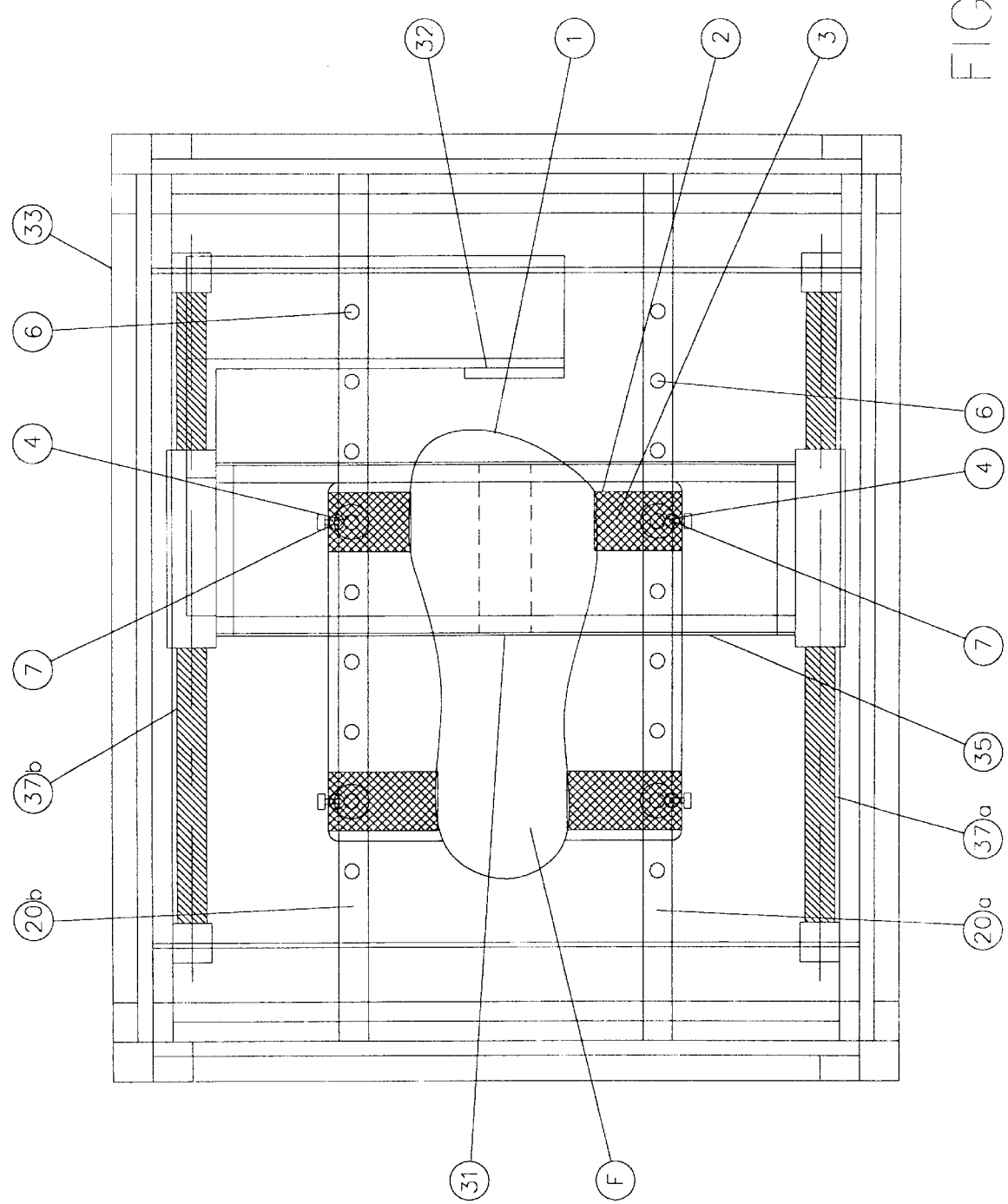
FIG. 3 is a top view of the foot supported and positioned by the device of the present invention, showing the upper head of a measurement system.

Once the foot to be measured is inserted into the envelope 10, it can be supported and positioned thanks to adjustable stems 4 each terminated by a pin 5. The pins 5 are provided with a narrow rounded tip 7 adapted for piercing a wing 2 at any appropriate location to set the envelope into a position that will in turn maintain the foot F in a desired position. As better seen in FIG. 2, the stems 4 are externally threaded at their lower end to be screwed in threaded through-holes 6 provided in support members 20a,b. Four to six stems or more can be positioned in any one of a series of threaded holes 6 as illustrated in FIG. 3, to provide the appropriate supporting structure to achieve the desired positioning of the foot F. Each stem 4 is preferably terminated by a pin assembly providing finer and faster adjustment of the vertical and horizontal position of the tip 7 of the pins 5. Each pin assembly comprises a bushing 8 sliding on the stem 4 and locked in a desired vertical and angular position using a thumb screw 9. The pin 5 is assembled on the bushing and has an externally threaded portion 11 on which a nut 12 is screwed. As seen in FIGS. 1 and 2, the nuts 12 are in intimate contact with the surface of wings 2 and provide an adjustable stop for final adjustment of the position of the envelope 10 and the foot F.

One can easily appreciate that the above described embodiment of the supporting and positioning device according to the present invention is simple and inexpensive, while it provides an effective solution to the need for accurate positioning of the foot for radiographic or scanning purposes and allows simultaneous scanning of the top and bottom surfaces of a foot F. The envelope is cheap to produce by dipping into a latex bath a core on which the strips of mesh material are removably attached. Therefore, each envelope can be used on one foot and threw away thereafter with no significant impact on the cost fabrication of an orthotic.

Typical applications of the device include positioning and maintaining the foot in the natural or neutral position, or in a position simulating for instance the morphology of the foot wearing a shoe with a heel of a specific height, for the purpose of collecting the dimensioning data required for designing a therapeutic insole (orthotic) or custom footwear. It shall be noted however, that while the invention provides very significant help in any foot supporting and positioning task, some such tasks will still require the specialist to further manipulate the foot to achieve the exact desired behaviour during the scan. Nevertheless, such a manual assistance will not require the use of force or induce fatigue and will usually not interfere with the scanning operation, providing useful data even when scanning of the top and bottom portions of the foot is carried-out simultaneously.

In order to provide a complete measurement system, a non-contact scanning system similar to some known technologies of the prior art can be integrated to the supporting and positioning device of the present invention. In FIGS. 1 to 3, a laser scanning system is shown integrated to the foot supporting and positioning device. Laser scanners 31 and 32 of the "fan" type, i.e. providing electronic sweeping such that a complete line can be scanned without moving the scanner head (see FIG. 2), are respectively mounted to scan the bottom and top portions of the surface of the foot F. Laser heads 31, 32 are mounted on a carriage 35, being assembled for movement on a pair of screws 37a,b driven by gears and motors enclosed in housing 33 along with a control system. The system is assembled on the supporting and positioning device through a set of structural members and comprises the usual hardware components for that type of system as would be obvious to one of ordinary skill in the field. The apparatus is further connected through a communication port 36 to a computer not shown providing control and image processing functions.

Therefor, it can be seen that the supporting and positioning device the present invention can be advantageously used to set a foot in a desired position for radiographic, optic or ultrasonic mapping of its physical characteristics with numerous advantages over the solutions of the prior art.

Although the present invention has been described by means of a preferred embodiment thereof, it is contemplated that various modifications may be made thereto without departing from the spirit and scope of the present invention. For example, the device could be used with equivalent advantages for the positioning of a hand for similar purposes. Also, any known type of non-contact measuring system could be used in co-operation with the device and could be mounted with significantly different hardware components without imparting the performance of the device according to the present invention. Accordingly, it is intended that the embodiment described be considered only as illustrative of the present invention and that the scope thereof should not be limited thereto but be determined by reference to the claims hereinafter provided and their equivalents.

What is claimed is:

1. A method for the acquisition of morphological data about a limb extremity, comprising the steps of:
   i. providing a thin stretchable envelope comprising positioning member engaging portions;
   ii. inserting the limb extremity into said thin stretchable envelope providing close fit;
   iii. attaching positioning members to said positioning member engaging portions in order to define a desired attitude of the limb extremity; and,
   iv. performing acquisition of morphological data about the limb extremity.

2. A method as recited in claim 1, further comprising the step of adjusting a position of said positioning members.

3. A method as recited in claim 1, wherein said acquisition of morphological data is performed by optical scanning.

4. A method as recited in claim 1, wherein said acquisition of morphological data is performed by three-dimensional scanning.

5. A method as recited in claim 1, wherein said step of acquisition of morphological data comprises simultaneous acquisition of data about a upper portion of the limb extremity and data about an underside portion of said limb extremity.

6. A method a recited in claim 1, wherein said limb extremity is a foot.

7. A method for the acquisition of morphological data about a limb extremity having an upper portion an underside portion, comprising the steps of:
   i. positioning the limb extremity in a desired attitude using a positioning device comprising a plurality of positioning members including a proximal end and a distal end; a thin stretchable envelope provided with portions for engaging the proximal end of said positioning members; and a supporting structure for engaging and immobilising the distal end of said positioning members; and,
   ii. using a scanning apparatus to map the three-dimensional relief of both the upper portion and the underside portion of said limb extremity substantially simultaneously, or sequentially without repositioning the limb extremity nor the positioning device before mapping is complete.

8. A system for the acquisition of morphological data about a limb extremity, comprising:
   a device for supporting and positioning the limb extremity in a desired attitude in view of performing acquisition of morphological data about the limb extremity, further comprising:
   a plurality of positioning members comprising a proximal end and a distal end;
   a thin stretchable envelope provided with portions for engaging the proximal end of said positioning members; and,
   a supporting structure for engaging and immobilising the distal end.

9. A device as recited in claim 8, wherein the position of the proximal end of at least some of said positioning members is adjustable with the distal end thereof remaining engaged in said structure.

10. A device as recited in claim 8, wherein said stretchable envelope has a pre-formed shape suitable to enable insertion onto a limb extremity and close conforming to the relief of predetermined portions of said limb extremity.

11. A system for the acquisition of morphological data about a limb extremity having an underside portion and an upper portion, said system comprising:
 a limb extremity positioning device comprising:
  i. a plurality of positioning members comprising a proximal end and a distal end;
  ii. a thin stretchable envelope provided with portions for engaging the proximal end of said positioning members; and,
  iii. a supporting structure for engaging and immobilising the distal end of said positioning members; and,
 a scanner having at least one head for scanning the relief of said underside portion, and me head for scanning the relief of said upper portion of the limb extremity.

12. A system for the acquisition of morphological data about a limb extremity as recited in claim 11, wherein said scanner is a three-dimensional optical scanner.

13. A system for the acquisition of morphological data about a limb extremity as recited in claim 11, wherein both scanning heads of said scanner operate simultaneously.

* * * * *